United States Patent [19]

Youlton

[11] Patent Number: 5,341,346

[45] Date of Patent: Aug. 23, 1994

[54] PORTABLE NARROW ANGLE SONAR RANGE FINDER

[76] Inventor: Francis W. Youlton, P.O. Box 938, Palo Alto, Calif. 94302

[21] Appl. No.: 106,517

[22] Filed: Aug. 16, 1993

[51] Int. Cl.$^5$ .................................................. G01S 15/00
[52] U.S. Cl. ..................................... 367/99; 367/138; 367/116
[58] Field of Search ................... 367/116, 103, 99, 138

[56] References Cited

U.S. PATENT DOCUMENTS

| | | | |
|---|---|---|---|
| 3,321,737 | 5/1967 | Russell | 367/116 |
| 4,310,903 | 1/1982 | Kay | 367/116 |
| 4,894,806 | 1/1990 | Jen et al. | 367/103 |
| 4,933,915 | 6/1990 | Bostrom | 367/99 |
| 4,937,796 | 6/1990 | Tendler | 367/116 |

*Primary Examiner*—Daniel T. Pihulic

[57] ABSTRACT

A small "flashlight" size pointing device for use as a sonar obstacle avoidance system for the blind. The apparatus comprises a bundle of small diameter tubes mounted in front of and perpendicular to the plane of a transducer. The transducer transmits sonic or ultrasonic pulses down the tubes which then spread out as a wave. Reflected waves, returning from obstacles are only detected by the transducer if they originate in a certain spatial beam area. This spatial beam area is controlled by the length and diameter of the tubes and by the transducer amplifier gain when used as a detector of reflected waves. Suitable values for the control variables result in reflections from obstacles only being detected in a spatial beam which can have a constant cross section independant of the distance of the reflecting object. For use as an obstacle avoidance system, repeated pulses are transmitted by the transducer and the delays between the transmitted pulse and the reception of the reflected wave are converted to audio tones.

12 Claims, 13 Drawing Sheets

```
*                   FIG 7a
*
*
* FILE - SONIC.ASM - PROGRAM TRANSMITS U/S WAVE
* TIMES REFLECTION AND OUTPUTS TONE DEPENDANT
* ON DISTANCE
* PROGRAM RESIDES IN EEPROM
regbas    equ      $1000
porta     equ      $0
portb     equ      $04
portc     equ      $03
* ram variables
          org      $00
dist      rmb      2
pn        rmb      1
lpn       rmb      1
*** start of program code.
          org      $b600
          lds      #$0047
          ldx      #regbas
next      ldaa     #0
          staa     portb,x   * initialize 'INIT' on
          jsr      wt        * u/s card
          jsr      wt
          jsr      wt
          jsr      wt
* send init/blnk signal with delay
          ldaa     #12
          staa     portb,x
          jsr      wt
* remove blnk signal
          ldaa     #4
          staa     portb,x
*** time return signal (1 to 53)
          ldy      #0
```

```
*                FIG 7b
*
*
t2        jsr      wt
          iny
          cpy      #53
          beq       ex
          ldaa     portc,x
          cmpa     #$fe
          beq      t2
ex        sty      dist    * load time into ram
**   put freq loop value into ram
          ldab     dist+1  * ram location for time
          ldx      #freq   * (1 - 53)
          abx
          ldaa     0,x
          staa     pn   * ram location for freq loop
          ldab     dist+1  * ram location for time
          ldx      #major
          abx
          ldaa     0,x
          staa     lpn     * ram location for
          ldx      #regbas * major loop
**  calculate #loops for 100ms+ timing
          ldab     dist+1
          cmpb     #1
          bne      l1
          ldy      #409
          bra      a2
l1        cmpb     #2
          bne      l2
          ldy      #390
          bra      a2
l2        cmpb     #3
          bne      l3
          ldy      #354
```

```
*                       FIG 7c
*
             bra     a2
13           cmpb    #4
             bne     14
             ldy     #324
             bra     a2
14           cmpb    #5
             bne     15
             ldy     #292
             bra     a2
15           cmpb    #6
             bne     16
             ldy     #281
             bra     a2
16           cmpb    #7
             bne     17
             ldy     #258
             bra     a2
17           ldx     #1t
             abx
             ldab    0,x
             ldy     #0
             aby
a2           ldx     #regbas
* 100 ms timing loop
             dec     dey
* positive half audio cycle
             bset    porta,x #$40
             ldaa    1pn
d2           ldab    pn
d1           decb
             cmpb    #0
             bne     d1
             deca
             cmpa    #0
```

```
*                   FIG 7d
*
            bne     d2
* negative or 0 half audio cycle
            bclr    porta,x #$40
            ldaa    lpn
d3          ldab    pn
d4          decb
            cmpb    #0
            bne     d4
            deca
            cmpa    #0
            bne     d3
** return to 100ms loop
            cpy     #0
            bne     dec
            jmp     next    *--- branch to init
* subroutine for 0.8 ms delay
wt          ldab    #$ff
d5          decb
            cmpb    #0
            bne     d5
            rts
** list of frequency loop delays
freq equ *
            fcb     33
            fcb     33
            fcb     17
            fcb     40
            fcb     14
            fcb     16
            fcb     54
            fcb     60
            fcb     68
            fcb     72
            fcb     82
```

```
*       FIG 7e                              FIG 7f
*
*
        fcb     91                  fcb     237
        fcb     103                 fcb     177
        fcb     110                 fcb     197
        fcb     122                 fcb     222
        fcb     137                 fcb     236
        fcb     147                 fcb     131
        fcb     165                 fcb     147
        fcb     184                 fcb     157
        fcb     103                 fcb     177
        fcb     110                 fcb     147
        fcb     122                 fcb     222
        fcb     138         major   equ     *
        fcb     147                 fcb     1
        fcb     166                 fcb     1
        fcb     184                 fcb     2
        fcb     208                 fcb     1
        fcb     221                 fcb     3
        fcb     246                 fcb     3
        fcb     184                 fcb     1
        fcb     197                 fcb     1
        fcb     221                 fcb     1
        fcb     246                 fcb     1
        fcb     82                  fcb     1
        fcb     88                  fcb     1
        fcb     98                  fcb     1
        fcb     110                 fcb     1
        fcb     117                 fcb     1
        fcb     133                 fcb     1
        fcb     147                 fcb     1
        fcb     166                 fcb     1
        fcb     177                 fcb     1
        fcb     197                 fcb     2
        fcb     221                 fcb     2
```

```
*         FIG 7g                          FIG 7h
*
*
          fcb    2                        fcb    40
          fcb    2               * list of 100ms
          fcb    2               * delay values
          fcb    2                 lt  equ  *
          fcb    2                        fcb    233
          fcb    2                        fcb    233
          fcb    2                        fcb    233
          fcb    2                        fcb    233
          fcb    3                        fcb    233
          fcb    3                        fcb    233
          fcb    3                        fcb    233
          fcb    3                        fcb    233
          fcb    10                       fcb    233
          fcb    10                       fcb    224
          fcb    10                       fcb    201
          fcb    10                       fcb    184
          fcb    10                       fcb    166
          fcb    10                       fcb    158
          fcb    10                       fcb    145
          fcb    10                       fcb    131
          fcb    10                       fcb    124
          fcb    10                       fcb    113
          fcb    10                       fcb    103
          fcb    10                       fcb    92
          fcb    15                       fcb    88
          fcb    15                       fcb    81
          fcb    15                       fcb    72
          fcb    15                       fcb    69
          fcb    30                       fcb    62
          fcb    30                       fcb    57
          fcb    30                       fcb    51
          fcb    30                       fcb    49
          fcb    40                       fcb    44
```

```
*       FIG 7i
*
*
        fcb     40
        fcb     39
        fcb     34
        fcb     31
        fcb     28
        fcb     26
        fcb     24
        fcb     22
        fcb     21
        fcb     18
        fcb     17
        fcb     15
        fcb     14
        fcb     13
        fcb     12
        fcb     11
        fcb     10
        fcb     9
        fcb     9
        fcb     8
        fcb     8
        fcb     8
        fcb     8
        fcb     8
        fcb     8
        fcb     8
***  end
```

PORTABLE NARROW ANGLE SONAR RANGE FINDER

FIELD OF THE INVENTION

This invention relates in general to sonic or ultrasonic sonar ranging systems and in particular to portable hand held obstacle detection sonar systems.

PRIOR ART

Ultrasonic range finders have been developed for many applications and their designs and the apparatus used have been disclosed in the prior art.

U.S. Pat. No. 4,280,204 by Gilbert M. Elchinger describes a dual mode ultrasonic obstacle detection sensor for use in a mobility cane for the blind. Adjustments in the direction of the sensor allow for the sensing of objects in various directions. However the spatial zone for the detection of obstacles, using the described method is relatively large. This would make it difficult for a user to negotiate a narrow path between obstacles by using the device. Signals would be continually returned from all directions and the spaces between obstacles would not be detected.

U.S. Pat. No. 4,464,738 by Stanislaw B. Czajkowski shows a sensing apparatus using a piezo electric transducer for radiating pulsed sonic or ultrasonic signals along a measured path, through a sound horn to create a narrow beam. An important feature of the apparatus is that the electronic circuitry includes an amplifier which will increase the amplification of the electrical signals carried by the reflected pulse as a function of time lapsed from the radiation of a measurement signal pulse so as to compensate for the attenuation of the received signal. Using various sizes of horns the sonic beam angle for detecting objects can be changed from 3 degrees to 20 degrees. However these angles are fixed for each horn and they do not change with the distance of the object. Different horns are needed for each angle and they are not continuously variable during use. In addition the horn systems are quite bulky.

The major limitation of these prior systems is in "sensing" the space between objects, as well as sensing the objects themselves. For example a blind person walking down a crowded street would like to be aware of obstacles and also of the gaps between them. That is they would like to negotiate a narrow path between obstacles. In addition equipment adjustable during use would allow immediate reaction, as the number of obstacles and their spacings change.

A more ideal hand held sonar ranging system, for obstacle avoidance, would detect obstacles within a spatial beam of adjustable width which would not change with the distance of the object from the device.

SUMMARY OF THE INVENTION

The principal object of this invention is to provide a more ideal portable sonic or ultrasonic obstacle avoidance system.

The preferred embodiment comprises a small, light, "flashlight" size pointing device, comprising of a bundle of small diameter tubes mounted in front of and with the axis of the tubes perpendicular to the plane of a transducer.

The apparatus operates by illuminating an area in front of the device with pulsed sonic or ultrasonic energy from the transducer. However reflected sonic or ultrasonic waves returning from obstacles are only received by a detection transducer if they come from obstacles within a certain spatial beam area. This beam's cross sectional area and its change with distance from the device is governed by certain design variables. These variables include (a) the sonic or ultrasonic pulse wavelength (b) the length of the individual tubes (c) the diameter of the individual tubes (d) the internal cross sectional and longitudinal profile of the tubes (e) internal tube coatings (f) the signal detection transducer amplifier gain (g) the change of the amplifier gain with time.

Suitable values for these variables can result in a spatial beam with an approximately constant cross section independent of distance, or a beam with an increasing or decreasing cross section. Typically the apparatus would be set to receive a reflected wave from the nearest object within a beam of one or two foot diameter cross section. The beam's cross section can be controlled during use either electronically or mechanically. This can be achieved by changing the amplifier gain or by using telescoping bundle of tubes.

For the preferred use of this apparatus as a hand held obstacle avoidance system, repetitive ultrasonic pulses are emitted by the transducer at a rate of between 4 and 10 per second. For each pulse the distance to the nearest pointed at obstacle is measured and this is converted to a range of audio frequencies varying from approximately 4000 cps for obstacles 1 foot away to approximately 50 cps for obstacles greater than 20 ft away. Other distances are prorated between these limits. The duration of the audio signals vary from 100 milliseconds at 4000 cps to 330 milliseconds at 50 cps.

BRIEF DESCRIPTION OF THE DRAWINGS

FIG. 7 is a print out of a typical microprocessor control program.

DESCRIPTION OF INVENTION

The preferred embodiment of the invention comprises a bundle of narrow tubes placed in front of and with the axis of the tubes perpendicular to the plane of a transducer. The transducer emits and receives ultrasonic or sonic pulses through this array of tubes.

Figure 1:
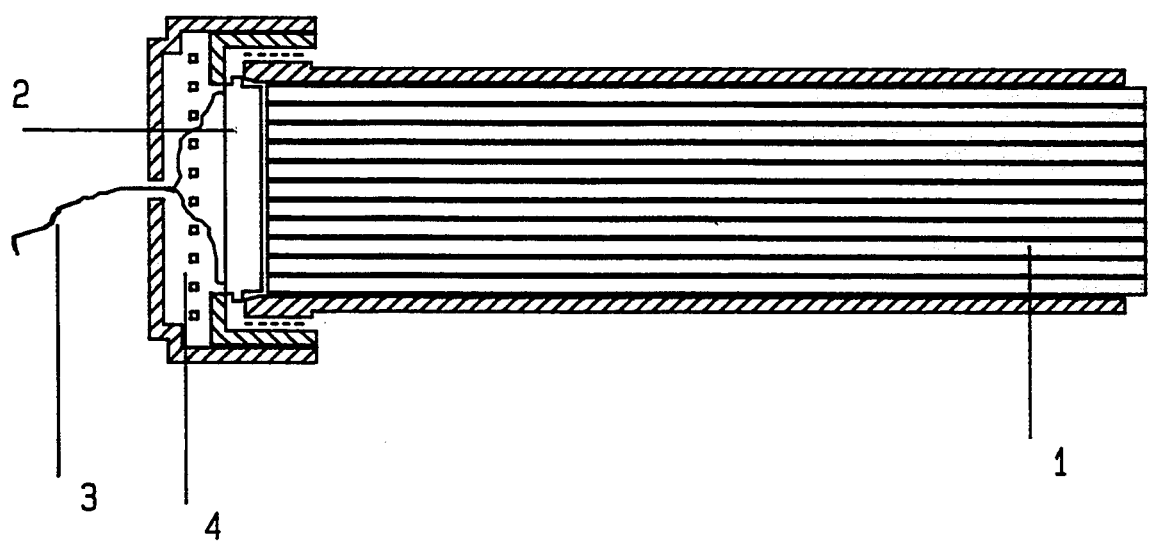
FIG. 1 of the drawings shows a cross section of the preferred embodiment of the hand held pointing device.
Figure 2:
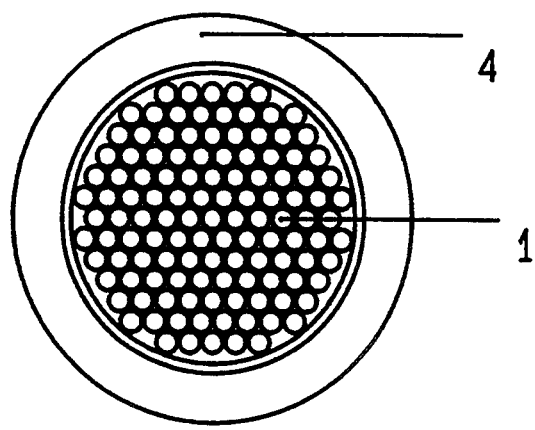
FIG. 2 shows a view of the end of the hand held device, looking down the open end of the bundle of tubes.

Refer now to FIG. 1 which is an overall drawing of the cross section of the preferred embodiment of the invention in which the transducer and tube system form a hand held pointing device for use as a sonar obstacle avoidance system. FIG. 2 shows an end view of the apparatus, looking down the open ends of the bundle of tubes.

The preferred embodiment comprises a 1.5 inch diameter bundle of ⅛th inch diameter hollow circular plastic stirring or drinking straws each of a fixed 5.5 inches long, FIG. 1 item 1. The bundle is mounted with the axis of the tubes perpendicular to the plane of a 1.5 inch 50 khz electrostatic transducer, FIG. 1 item 2. An end cover, FIG. 1 item 4 allows for air cooling of the transducer. This avoids overheating during high repetitive pulse rates. Two wires from the transducer, FIG. 1 item 3, allow connection of the transducer to the control circuitry.

It is believed that the invention operates as follows: A short duration sonic or ultrasonic pulse from the electrostatic transducer is transmitted as a plane wave down the narrow plastic tubes. On reaching the end of the tubes some energy is reflected back toward the transducer but the majority leaves the end of the tubes and spreads out as a wave. This wave then impinges on any obstacle in its path and a portion of the energy is reflected back toward and through the bundle of tubes to the transducer. The angle at which the reflected waves enter the tubes depends on the position of the obstacles. Obstacles more to the side of where the tubes are pointing reflect waves which enter the bundle of tubes at more acute angles.

When the reflected wave enters the tubes at an angle, multiple internal reflections occur as the wave travels back toward the transducer. The number of internal reflections depends on the entry angle.

The fraction of the reflected wave energy absorbed in the bundle of tubes depends on the tube material and the angle of incidence of the beam.

The wave energy reaching the transducer therefore depends on the energy of the wave entering the tube, which is a function of the distance of the reflecting object, and on the number of internal reflections, if any, within the tubes. This energy is detected by the transducer if the amplified signal is above a certain threshold value, which depends on the gain of the transducer amplifier.

Combining these factors results in an equation of the form shown below for the first order effects:

$$IC < (k) \times (AG) \times \left(\frac{1}{d^2}\right) \times S^{(\frac{L}{2a} \tan(g))}$$

where
IC = detection threshold
k = a constant
AG = transducer amplifier gain
d = distance of reflecting object
S = constant, depends on the tube material
L = length of the tubes
a = radius of the tubes
g = angle from the tube axis at which the wave enters the tube The amplifier gain can be made a function of time such that the longer the transducer waits for the return of the reflected wave the higher the amplifier gain. This gain then depends on how far the obstacle is from the tubes. The impact of such a change would be to make "AG" a function of "d" in the above equation.

The variables controlling the cross section of the spatial beam versus distance of the obstacle, for the returned reflections from the obstacle to be detected are:

a) The length of the individual tubes.
b) The diameter of the individual tubes.
c) The tube material.
d) The distance of the obstacle.
e) The strength of the emitted pulse.
f) The transducer area.
g) The gain of the transducer amplifier.
h) The rate of change of the amplifier gain.
i) The angle the reflected wave from the obstacle makes with the axis of the tubes.

Figure 3:
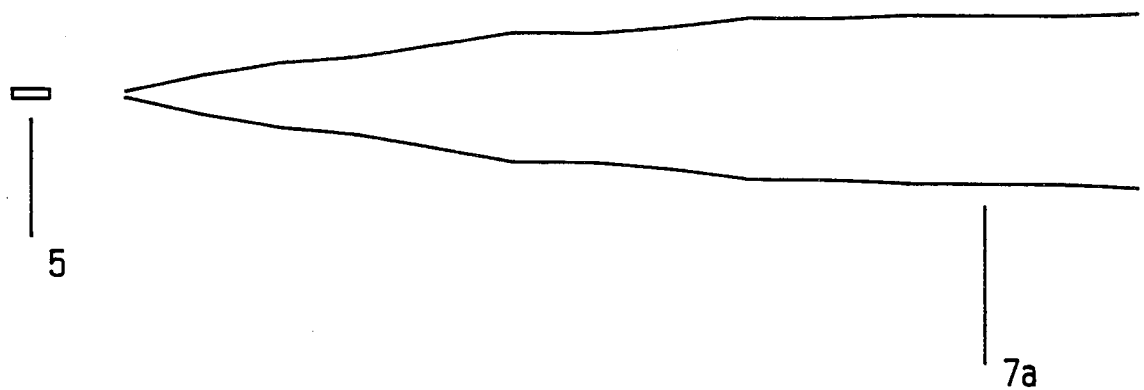
FIG. 3 shows the longitudinal cross section of the spatial beam for the preferred embodiment of the invention as an obstacle avoidance sonar system. Obstacles in this beam would be detected.
Figure 4:
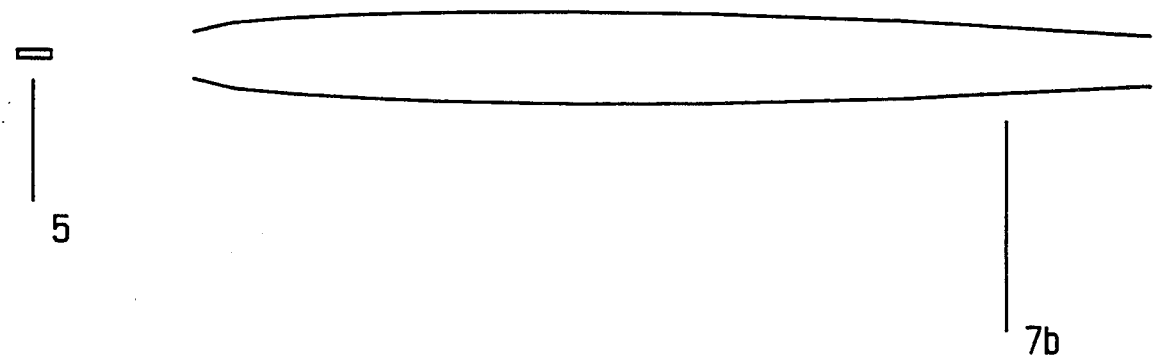
FIG. 4 is a view of the longitudinal cross section of the spatial beam for a more parallel beam implementation of the invention.

The preferred embodiment of the invention includes either a fixed transducer amplifier gain or an amplifier gain which increases by 50× during the time it takes the ultrasonic pulse to travel to and from an obstacle approximately 20 feet away. FIG. 3 is a view of the spatial beam's longitudinal cross section, in which obstacles are detected, for an amplifier gain of 50×. FIG. 3 Item 1 represents the transducer and tube bundle, while FIG. 3 item 2 points to the spatial beam longitudinal cross section in which reflections from obstacles are detected. FIG. 4 is similar to FIG. 3 except this represents the case of a constant amplifier gain.

Suitable selections for the values of the variables can lower the beam angle, for obstacles to be detected, down to a fraction of a degree. Typically this would involve using plastic tubes 12 inches long and ⅛ inch diameter.

Many of these controlling variables can be changed in real time operational use, either manually or automatically. For example a manually variable amplifier gain in the transducer detection circuit would allow the shape of the reflected spatial beam, which is detected by the transducer to be controlled. An apparatus which incorporates a telescoping tube system, whereby the overall length of the bundle of tubes can be changed over a continuously variable range, can also be used to change the detected spatial beam's longitudinal cross section in which reflected waves are detected by the transducer. In addition the effective strength of the emitted sonic or ultrasonic pulse in the detection area can be increased by mounting a flange or a concave reflector, of a few inches in diameter, at the open end of the bundle of tubes.

Modifications to the preferred embodiment of the apparatus can be made to improve on the basic design trade off between the emitted ultrasonic or sonic energy and the threshold of detection of the reflected waves. The stronger the emitted wave, the greater the distance from which reflected waves are returned with an energy above the detection threshold. The higher the energy of the reflected waves the wider the cross sectional spatial beam area from which reflections are detected. That is there is a trade off between the emitted energy and the width of the reflected beam within which obstacles are detected. This trade off can be more optimized by designing the bundle of hollow tubes to absorb more of the wave energy from reflected waves which are at wide angles from the axis if the tubes. Such tube designs would include internal coatings with a sound absorbing material, using an absorbing tube material or changing the cross sectional area and shapes and the internal and external profiles of the tubes, for example to include baffling designs.

An additional method of achieving a more optimum solution to the above design trade off would be to use two transducers, one of which repeatedly emits ultrasonic or sonic pulses while the second transducer is used as a receiver of reflected waves and has a bundle of hollow tubes mounted with the axis of the tubes perpendicular to the plane of the transducer.

Extensions of the preferred embodiment of the apparatus design include adding scanning mechanisms to the transducer and tube assembly of the hand held device or by the use of arrays of transducer tube detector systems.

In the case of scanning systems using the two transducer design, one transducer repeatedly emits ultrasonic or sonic pulses and after each transmission the apparatus waits until a reflected wave has been received, or for a maximum time. The transducer system then rotates to point to a new direction and emits the next sonic or ultrasonic pulse. For each pulse, in each direction, the reflected wave is received by the second transducer which has a bundle of tubes mounted with the axis of the tubes perpendicular to the plane of the transducer.

The above design can be modified such that the two groups of transducers are reduced to a single transducer, the receiver transducer with the bundle of tubes, which acts as both the emitter of sonic or ultrasonic pulses and the detector of reflected waves.

Arrays of transducer emitter and transducer tube detector systems would comprise two groups of transducers, an emitting group composed of one or more transducers and a receiving group composed of one or more transducers mounted so as to receive reflected waves from different spatial beam directions. The emitting group of transducers emits ultrasonic or sonic pulses and after each transmission waits until all the receiving transducers have detected a reflected wave or for a maximum time and then the emitting transducers emit the next pulse. The reflected waves are received by the second group of transducers, each of which has a bundle of hollow tubes mounted with the axis of the tubes perpendicular to the plane of the transducer. The above design can be modified so that the two groups of transducers are reduced to a single group of transducers, the receiver transducers each with a bundle of tubes, which act as both the emitter of sonic or ultrasonic pulses and detector of reflected waves.

Scanning or array systems can be particularly useful for autonomous robot vehicles where the distance of the nearest object in each scan or transducer array position is used for determining the distance profile of any object, to the spatial accuracy required, in the path of an autonomous vehicle. This profile being used to determine whether the object is a convex corner, a concave corner, a flat wall, an isolated object or a series of objects and spaces or any other shape. The information is then used by the vehicle in making a decision on which direction to travel. Much of the circuitry for emitting sonic or ultrasonic pulses and timing the returned signals is covered in the prior art, and many of the subcomponents are available commercially. However in the preferred embodiment of the apparatus, as an obstacle avoidance sonar system for the blind, the key feature is the method of communicating the distance information collected by the apparatus.

In the preferred embodiment repetitive ultrasonic pulses are emitted by the transducer at a rate of between 4 and 10 per second. For each pulse the distance from the nearest pointed at obstacle is measured and this is converted to a range of audio frequencies varying from approximately 4000 cps for obstacles 1 foot away to approximately 50 cps for obstacles greater than 20 ft away. Other distances are prorated between these limits. The duration of the audio signals vary from 100 milliseconds at 4000 cps to 330 milliseconds at 50 cps. The emitted pulses are frequent enough to detect approaching objects and the short audio tones of 100 millisecond duration at a high frequency give a sense of urgency for close objects. The audio amplifier transmits the audio tone to the headphones.

Figure 5:
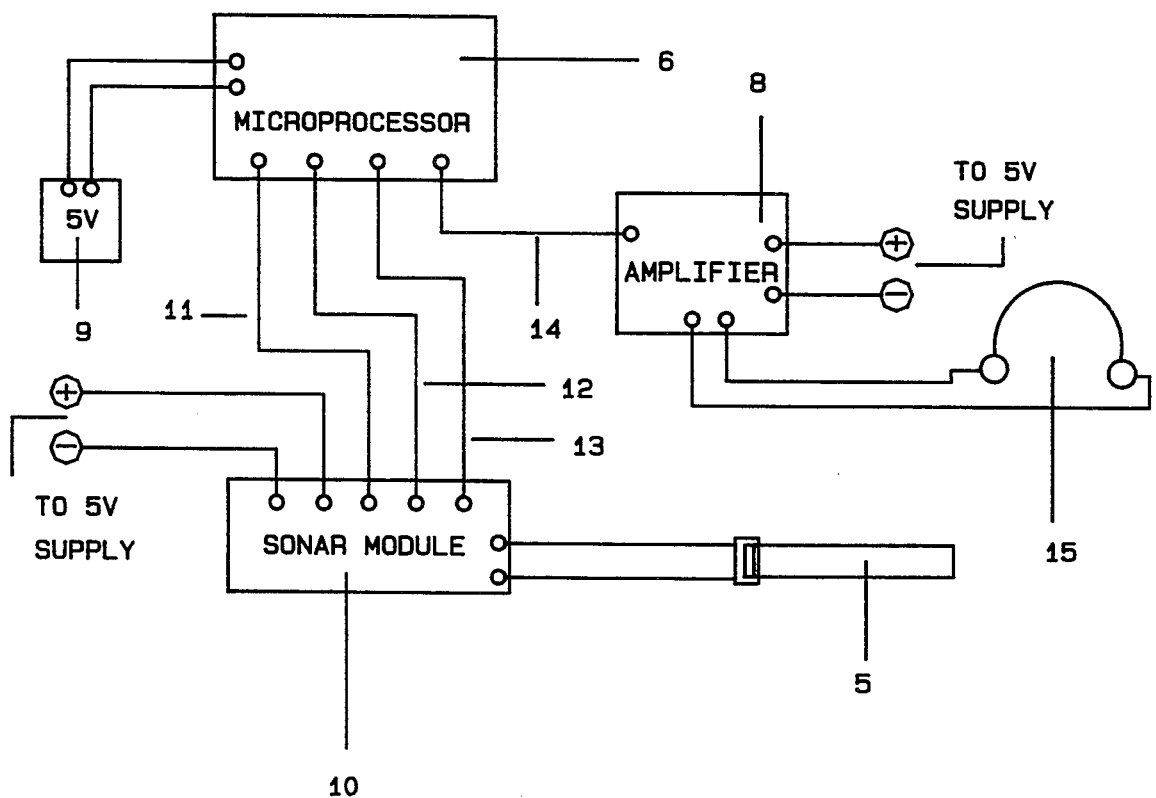
FIG. 5 is a block circuit diagram for the overall measuring and display system.

The block diagram for the preferred circuit is shown in FIG. 5. It comprises a microprocessor such as a Motorola M68HC11 FIG. 5 item 1, a transducer ranging module such as the Texas Instruments TL851/TL852 system FIG. 5 item 4, an amplifier FIG. 5 item 2 and set of headphones FIG. 5 item 6. Power is provided by 4 AA batteries FIG. 5 item 3. FIG. 5 Item 5 represents the transducer and tube bundle. In operation the microprocessor output lines FIG. 5 items 7 and 8 apply positive potentials to the pulse initiation and signal blanking connections of the sonar module. After approximately 1 millisecond the blanking potential line is returned to ground by the microprocessor. On application of the initiation potential to the sonar module a short burst of 50 khz ultrasonic energy is transmitted down the narrow tubes by the transducer. The blanking signal prevents energy reflected from the open ends of the tubes from being received by the transducer.

When the first 50 khz returning reflected pulse reaches the transducer the "echo" line of the sonar module goes high FIG. 5 item 9 and this is detected by a microprocessor input line. The time between raising the potential on the initiation line by the microprocessor and the echo input line of the microprocessor going high is measured by the microprocessor. This time is proportional to the distance of the nearest object. Based on this time, a sequence of alternating positive and ground signals are sent to an amplifier from an output line of the microprocessor FIG. 5 item 10, at a frequency and for the durations described earlier. On completion of this sequence the microprocessor returns the initiation line to ground and then repeats the process again by returning the initiation line positive.

FIG. 7 is a listing of the microprocessor control program.

Figure 6:
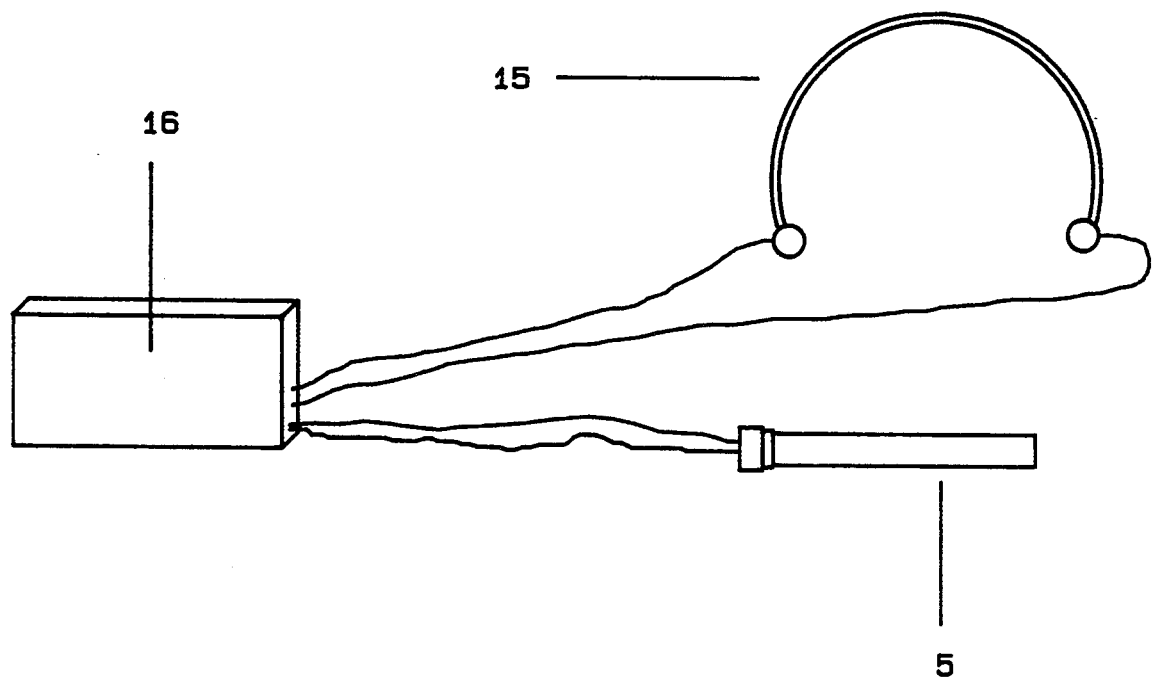
FIG. 6 is an overall view of the portable object avoidance system showing its three major components for the preferred embodiment of the system.

The overall preferred embodiment of the portable narrow angle sonar range finder system is shown in FIG. 6. FIG. 6 item 1 shows the hand held device, FIG. 6 item 2 is belt mounted, and contains the control electronics. FIG. 6 item 3 shows the headphones for providing the audible tones.

Variations in the preferred embodiment for the design of the hand held obstacle avoidance system include an apparatus in which the hand held pointing device contains controls to change the transducer amplifier gain and or to control the length of telescoping bundle of tubes. This would allow the spatial beam's cross section, in which reflected sonic or ultrasonic waves are detected to be changed during use. The apparatus could also be designed wherein the total system including the transducer control system is incorporated into the hand held device.

Many display methods can be used to display the obstacle distance information other than audible tones. These would include, for example:

a) The time between the emission of the sonic or ultrasonic or sonic pulses and the detection of the reflected wave is displayed as a spoken distance rather than a audio tone.

b) The time between the emission of the ultrasonic or sonic pulses and the detection of the reflected wave is displayed as the length of a rod above a plane surface, the rod movement being controlled by the microprocessor. Another variation to this display method would include a braille output. These types of display would be appropriate for deaf people.

Display methods for the obstacle distances for scanning systems or transducer array systems would include, for example:

a) The object distances measured for each scan or array position by each receiving transducer is displayed as a three dimensional sound pattern, such that the relative loudness of the tone in each ear depends on the direction of the tube or array position and the average loudness and frequency depends on the distance of the reflecting object.

b) Only the tones for the nearest and or the furthest object are sounded according the 3 dimensional positions of these objects as described in (a) above. This method overcomes the problem of too much continuously changing information being provided to the user in a way which makes interpretation extremely difficult.

c) A display method in which a topography map is produced, for example, by an array of rods or equivalent where the length of each rod, for each array position depends on the on the distance of the nearest reflecting object in the equivalent scan or transducer array position.

The use of a bundle of narrow tubes through which a transducer receives sonic or ultrasonic waves reflected from obstacles provides a method for increasing the resolution of sonar ranging systems. The shape of the beam within which obstacles are detected can be controlled during use and the small, light, flashlight size of the apparatus provides a more ideal hand held sonar ranging system.

The foregoing description of the preferred embodiment of the invention has been presented for the purpose of illustration and description. It is not intended to be exhaustive or limit the invention to the precise form disclosed. Many modifications and variations are possible in the light of the above teaching. It is intended that the scope of the invention be limited not by this detailed description but rather by claims appended hereto.

I claim:

1. A sonar ranging obstacle avoidance system with a variable narrow obstacle detection spatial beam comprising:

a bundle of hollow tubes mounted in front of the plane of a transducer, which transducer has means for emitting sonic or ultrasonic pulses and means for detecting reflected sonic or ultrasonic waves which have an energy above a certain detection threshold;

means for measuring the time between the emission of a sonic or ultrasonic pulse by the transducer and the detection of reflected sonic or ultrasonic waves;

means for converting this said measured time to the distance travelled by the sonic or ultrasonic pulse during this time;

means for displaying this distance; said transducer repeatedly emits sonic or ultrasonic pulses which then travel down the said tubes and leave the end of the tubes and spread out as a wave, any of the said wave which is reflected back from an obstacle toward and through the said tubes to the transducer is detected by the transducer detection means if it is above the said certain energy value of the transducer detection means, and the time between the emission of the ultrasonic or sonic or pulses and the detection of the reflected waves by the transducer is measured by the said transducer time measuring means and converted to a said distance which is then displayed by the said display means; said wave's energy after passing through the said tubes is dependant on the absorption of the said reflected wave in the said tubes, and which absorption also depends on the angle the said reflected wave makes with the axis of the said tubes and only such waves that are reflected within a range of certain said angles, and certain distances from the axis of the tubes and certain distances of the reflecting object from the tube bundle, have an energy above the said certain detection threshold of the said transducer detection means, which transducer will therefore only detect reflections from objects which are within a certain shaped narrow spatial beam in front of the bundle of tubes and around the extended axis of the tubes, which spatial beam's shape is predetermined by the length of the individual said tubes, the diameter of the individual tubes, the tube material, internal tube coatings, the cross sectional and longitudinal profile of the tubes, the sonic or ultrasonic wavelength and the said certain energy value of the transducer detection means.

2. An apparatus according to claim 1 wherein the tubes in the bundle are all the same length and of a circular cross section and are mounted with the axis of the tubes in front of and perpendicular to the plane of the transducer.

3. An apparatus according to claim 1 wherein the transducer emits a sonic or ultrasonic pulse and after the transducer's wave detection means has detected a reflected wave, then said apparatus rotates to point to a new direction and the sequence of pulse emission, detection and rotation continues.

4. An apparatus according to claim 1 in which the transducer and tube system form a hand held device for use as a sonar obstacle detection system.

5. An apparatus according to claim 1 wherein the transducer reflected wave detection means includes an amplifier having a variable gain, which gain modifies the detection threshold energy value above which the reflected wave is detected, thereby allowing the shape of the reflected spatial beam, which is detected by the transducer to be changed and controlled.

6. An apparatus according to claim 1 in which the bundle of tubes have telescoping means, whereby the length of the tubes in the bundle can be continuously changed over a predetermined range, thereby allowing the shape of the reflected spatial beam, which is detected by the transducer, to be changed.

7. An apparatus according to claim 1 in which the sonar ranging obstacle avoidance system comprises a hand held device wherein:

the transducer reflected wave detection means includes an amplifier with a variable gain;

the bundle of tubes have telescoping means whereby the length of the tubes can be continuously changed over a predetermined range;

the device includes controls to change the gain of the amplifier and the length of the tubes, where these said controls allow the spatial beam's cross sectional area, in which reflected sonic or ultrasonic waves are detected, to be changed during use.

8. A sonar ranging apparatus with a variable narrow obstacle detection spatial beam resolution, comprising:
two groups of transducers, an emitting group which have means for emitting sonic or ultrasonic pulses and a receiving group, which transducers have means for detecting reflected sonic or ultrasonic waves which have an energy above a certain detection threshold and said receiving group of transducers have bundles of hollow tubes mounted in front of the plane of each of the transducers and said receiving transducers are mounted so as to receive reflected waves from different spatial directions;
means for measuring the time between emission of an sonic or ultrasonic pulse by each of the transducers in the emitting group of transducers and detection of reflected ultrasonic waves by the receiving transducers;
means for converting these said measured times to the distances travelled by the sonic or ultrasonic pulse during these times;
means for displaying these distances;
the said emitting group of transducers repeatedly emit ultrasonic or sonic pulses which spread out as waves, and any of the said waves which are reflected back from an obstacle toward and through the said tubes to the said receiving transducers is detected by the receiving transducer's detection means, if it is above the said certain detection threshold energy values of the receiving transducers and the time between the emission of the ultrasonic or sonic pulses and the detection of the reflected waves by the said receiving transducers detection means is measured by the said receiving transducers time measuring means and converted to said distances, one for each receiving transducer and which distances are displayed by the said display means; said reflected wave's energy value after passing through the said tubes is dependant on the absorption of the said reflected wave in the said tubes; said tube system attenuates the wave energy incident on the transducer, depending on the absorption within the tubes, and which absorption also depends, on the angle the said reflected wave makes with the axis of the said tubes and only such waves that are reflected within a range of said angles, and certain distances from the axis of the bundle of tubes and certain distances of the reflecting object from the tube bundle, have an energy above the said certain detection threshold of the detection means, which apparatus will therefore only detect reflections from objects which are within a shaped spatial beam in front of the bundle of tubes relative to the extended axis of the tubes, which spatial beam's shape is predetermined by the length of the individual tubes, the diameter of the individual tubes, the tube material, internal tube coatings, the cross sectional and longitudinal profile of the tubes, the sonic or ultrasonic wavelength and the said certain detection threshold of the transducers detection means.

9. An apparatus according to claim 8 where the time between the emission of the sonic or ultrasonic pulses by the emitting transducers and the detection of the reflected waves by the receiving transducer's reflected wave detection means is displayed as a three dimensional pattern.

10. An apparatus according to claim 8 wherein the apparatus comprises a hand held device wherein:
the transducer reflected wave detection means includes amplifiers with a variable gain;
the bundle of tubes have telescoping means whereby the length of the tubes can be continuously changed over a predetermined range;
the device includes controls to change the gain of the amplifier and the length of the tubes where these said controls allow the spatial beam's cross sectional area, in which reflected sonic or ultrasonic waves are detected, to be changed during use.

11. An apparatus according to claim 8 wherein the emitting transducers emit a sonic or ultrasonic pulse and after the receiving transducer's wave detection means have detected a reflected wave, then said apparatus rotates to point to a new direction and the sequence of pulse emission, pulse detection and rotation continues.

12. An apparatus according to claim 8 where the tubes in the bundle are all the same length and of a circular cross section and are mounted with the axis of the tubes in front of and perpendicular to the plane of the transducer.

* * * * *